United States Patent [19]  [11] Patent Number: 5,071,403
Larsson  [45] Date of Patent: Dec. 10, 1991

[54] METHOD AND APPARATUS FOR PROTECTING THE PUMP OF A BREAST PUMP FROM FOULING BY MILK

[75] Inventor: Karl O. A. H. Larsson, Schweiz, Switzerland

[73] Assignee: ISG/AG, Zug, Switzerland

[21] Appl. No.: 436,381

[22] Filed: Nov. 14, 1989

[51] Int. Cl.$^5$ .............................................. A61M 1/06
[52] U.S. Cl. ...................................... 604/74; 604/320
[58] Field of Search ...................................... 604/73–76, 604/313, 315, 346, 119, 320

[56] References Cited

U.S. PATENT DOCUMENTS

| | | | |
|---|---|---|---|
| 2,162,076 | 6/1939 | Frimand | 604/74 |
| 4,740,202 | 4/1988 | Stacey et al. | 604/119 |
| 4,794,915 | 1/1989 | Larsson | 128/64 |
| 4,813,931 | 3/1989 | Hauze | 604/54 |
| 4,857,051 | 8/1989 | Larsson | 604/74 |
| 4,886,494 | 12/1989 | Morifuji | 604/74 |
| 4,915,691 | 4/1990 | Jones et al. | 604/73 |
| 4,929,229 | 5/1990 | Larsson | 604/74 |

OTHER PUBLICATIONS

Maier, W. DT-OS-2658322, Filed 12/22/76, Published 6/29/78.

Primary Examiner—John D. Yasko
Assistant Examiner—Adam J. Cermak
Attorney, Agent, or Firm—Willian Brinks Olds Hofer Gilson & Lione

[57] ABSTRACT

Method and apparatus for restricting the passage of milk beyond a selected place in breast pump apparatus and for protecting the pump from fouling by milk. A barrier to the passage of human milk is disposed in an air passage interconnecting the vacuum pump and a breast-contacting hood or the like for receiving expressed milk. In conventional fashion, operation of a vacuum pump may result in the expression of milk into the hood, where it may be collected. The air being drawn toward the vacuum pump passes through a porous body that is normally substantially permeable to air. The porous body is impermeable to human milk. Accordingly, it serves as a barrier across the vacuum line and protects the pump. When contacted by human milk, the porous body becomes substantially impermeable to air, at least at the point of contact. Depending upon the extent of such contact, the amount of vacuum that reaches the interior of the hood is reduced or eliminated, thereby reducing or eliminating the further expression of milk.

14 Claims, 2 Drawing Sheets

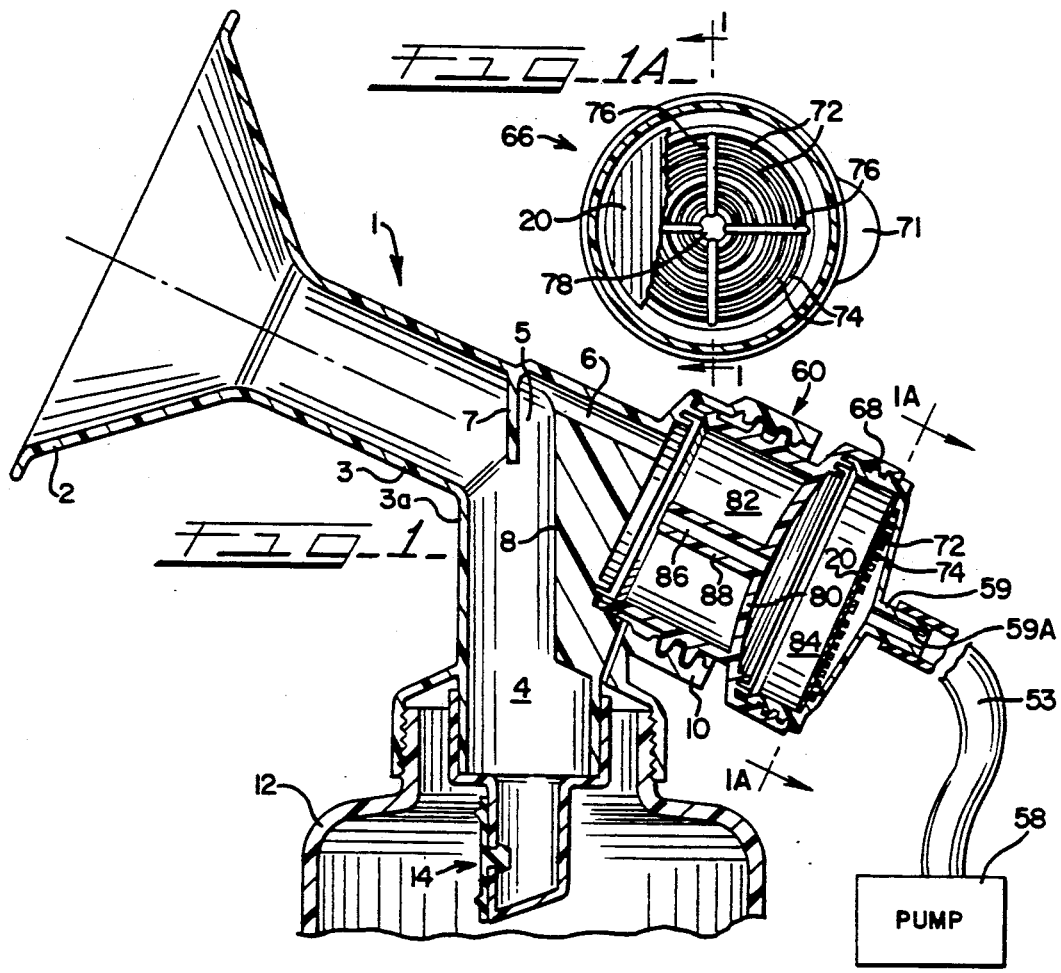
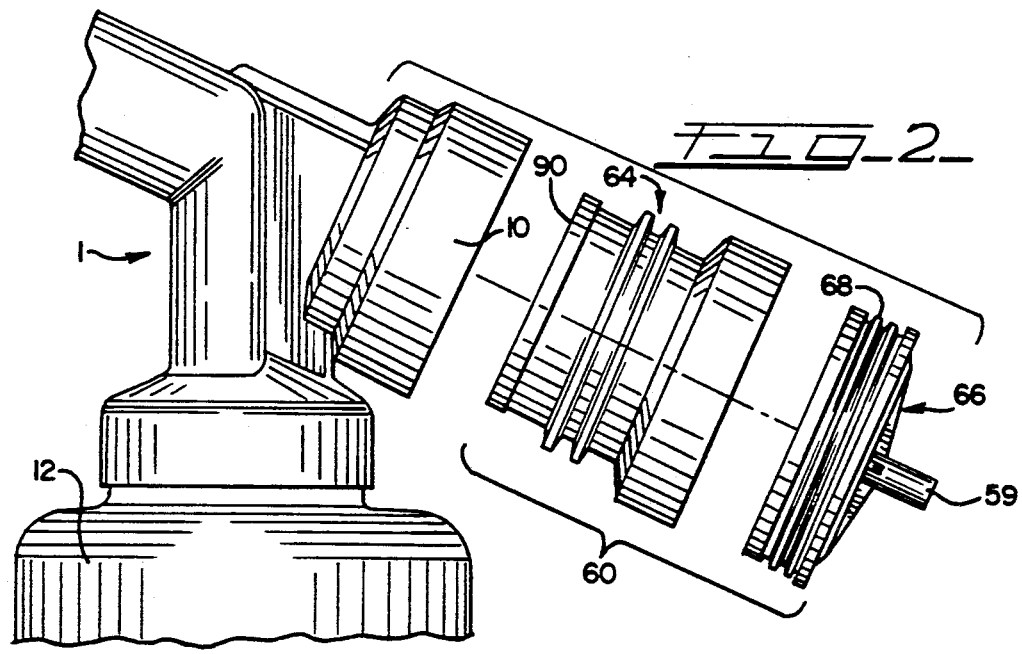

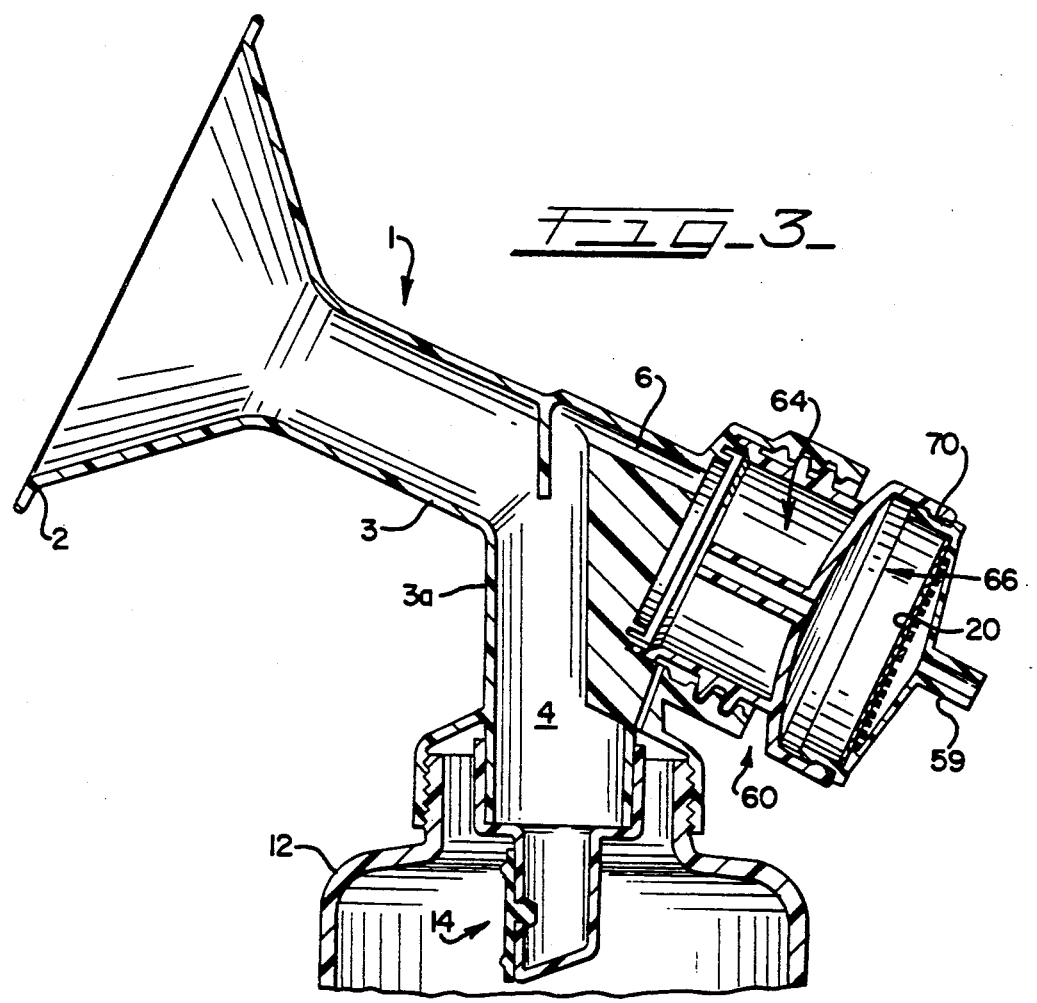
FIG_3_
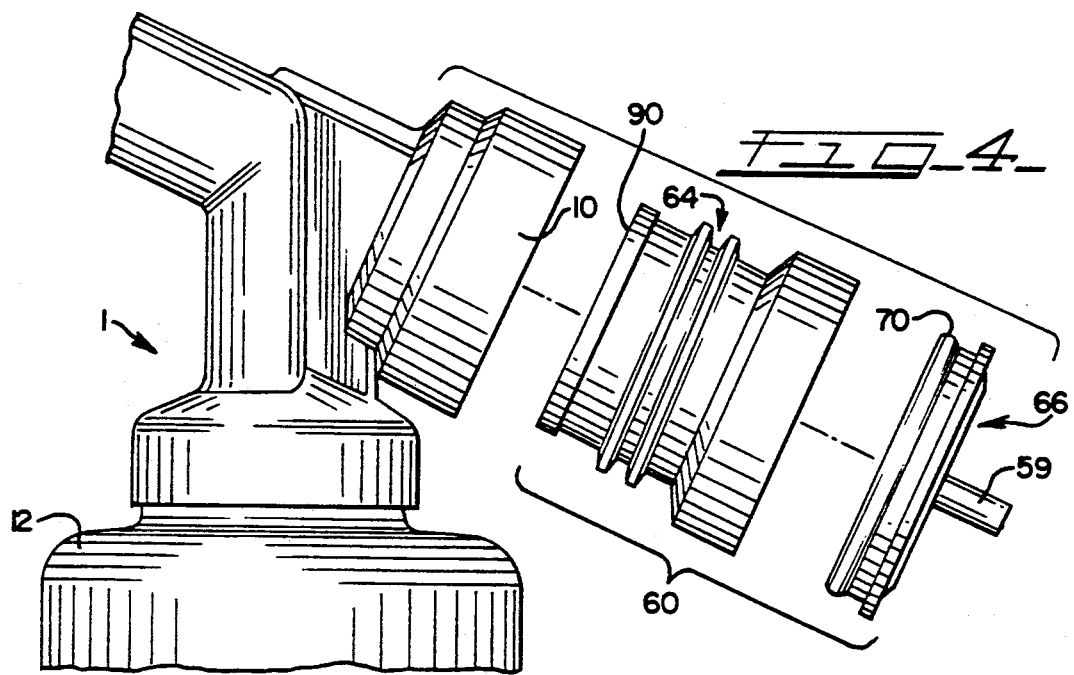
FIG_4_

METHOD AND APPARATUS FOR PROTECTING THE PUMP OF A BREAST PUMP FROM FOULING BY MILK

FIELD OF THE INVENTION

The present invention relates to breastmilk pumps, and more particularly relates to new method and apparatus for protecting the pump portion of breast pump apparatus from contact by milk which otherwise might be drawn toward the pump through the vacuum line, or its equivalent, that connects the pump and the hood portion of the breast pump.

BACKGROUND OF THE INVENTION

Breast milk pumps are well-known, and generally comprise a hood that fits over the breast, a vacuum pump connected to the hood for generating an intermittent vacuum within the hood, and a receptacle for the expressed milk. Manually driven vacuum pumps as well as those that are driven by a motor are commonly used. The vacuum pumps of these devices, as a rule, intermittently generate a vacuum or negative pressure within the hood, with the hood encompassing the nipple and a substantial amount of the breast. The intermittent suction action of the pumps serves to pull on the breast and thereby extract milk in an action reminiscent of suckling. The milk so extracted typically flows from the hood into a collection container for storage and later use.

The disclosure of my U.S. Pat. No. 4,857,051 is hereby incorporated by reference. It discloses embodiments of breast pumps and methods of operating breast pumps suitable for use with the current invention. Milk expressed into a body hood or hood member under the operation of a manual or electric vacuum pump is collected in a container.

The disclosure of my U.S. Pat. No. 4,794,915 also is hereby incorporated by reference. It relates to a method for the stimulation of the nipples of the breasts of a pregnant woman in order, among other things, to enhance the production of labor-inducing hormones and to enable the performance of contraction stress-tests. This method often produces milk, sometimes in large volume. Therefore, it is also suitable for use with the current invention.

As noted in the above-incorporated U.S. Pat. No. 4,857,051, one significant failing of previous devices was that the milk expressed often reached the vacuum line or even the pump. In order to eliminate such a serious problem, many devices contain so-called safety volumes between the hood and the pump. Such a solution of the problem is expensive and usually cannot provide effective protection of the vacuum line and pump from milk. Also, varying degrees of the vacuum can be generated as the milk receptacle fills, which must then be compensated for.

In order to address these and other problems, U.S. Pat. No. 4,857,051 discloses a hood body or member to which a collecting or catch chamber is connected. At the outlet of the collecting chamber there is provided a valve which closes a passage leading from the collecting chamber to a receiving container. When a vacuum or negative pressure is applied to the hood from a suction device, the valve closes the collecting chamber outlet to the receiving chamber, but opens the outlet on the return cycle of the pump to force the milk expressed from the collecting chamber into the receiving chamber. A baffle arrangement is further described in conjunction with the valve mechanism in an attempt to prevent milk from passing into the vacuum line or from reaching the vacuum pump. In the disclosed embodiments, the baffle arrangement comprises a trap in which a separation wall 7 and a rear wall B form a vacuum passage 5 therebetween.

It has been discovered that a trap such as the type formed by the disclosed baffle arrangement may sometimes be less than completely effective in preventing milk from entering the vacuum line or reaching the pump. For example, it is possible for milk to be produced in such volume that it overflows the collecting or catch chamber 4 and overflows the trap, entering vacuum line 6. Such results may be encountered when using a stimulating technique such as disclosed in the above-incorporated U.S. Pat. No. 4,794,915. Accordingly, a more effective apparatus and method is needed to protect the vacuum pump and any associated hose or the like.

SUMMARY OF THE INVENTION

An object of the current invention is to place a physical barrier to the passage of milk within the air path itself that interconnects the vacuum pump and the hood. The barrier permits sufficient fluid communication between the vacuum pump and the hood during normal operation for the apparatus as a whole to perform its intended function. Should milk reach the barrier and make contact with the barrier, the barrier serves to protect the vacuum pump and downstream portions of the air path from further encroachment by the milk.

In its presently preferred embodiment, the barrier takes the form of a porous body, most preferably a filter in the form of a washable element. The porous body is disposed across the fluid connection between the vacuum pump and the hood such that air being withdrawn by the pump passes through the porous body, which is normally substantially permeable to air.

The porous body is substantially impermeable to human milk, at least at pressures of the magnitudes commonly generated by the vacuum pumps in breast pump apparatus. Accordingly, when milk reaches the porous body and wets it, air may no longer pass through the porous body, at least where the porous body is wet. At least to the extent that the porous body is wet with milk, the flow of air toward the source of vacuum is reduced.

The consequent decrease in vacuum within the hood is felt by the nursing mother, who becomes aware that a change has occurred. If she has been instructed as to what that means, she may take corrective steps. Even if not, the pump will still be protected.

In light of the above, the current apparatus and method properly may be described either as presenting a physical barrier to the passage of milk, thereby protecting the downstream apparatus, or as halting or reducing the continued flow of air toward the vacuum pump, thereby protecting the downstream apparatus.

It is presently preferred for the current invention to be implemented by placing the porous body in a housing that can be removably connected to a variety of apparatus, both for the sake of enhanced universality of application and for ease of cleaning. Most preferably, the housing is openable for cleaning the housing and the washable porous body. For this purpose, I prefer to construct the housing from two separable bodies held together by a releasable connection such as screw threads or the like.

BRIEF DESCRIPTION OF THE DRAWINGS

FIG. 1 is an elevation in cross-section of a representative hood of breast pump apparatus, provided with a presently preferred embodiment of a porous body in a first embodiment of a housing;

FIG. 1A is a view taken along line 1A—1A of FIG. 1, with the porous body partially broken away;

FIG. 2 is an exploded elevation of the apparatus of FIG. 1;

FIG. 3 is an elevation in cross-section of a representative hood of breast pump apparatus, provided with a presently preferred embodiment of a porous body in a second embodiment of a housing; and FIG. 4 is an exploded elevation of the apparatus of FIG. 3.

DETAILED DESCRIPTION OF EMBODIMENTS OF THE INVENTION

Turning now to FIG. 1, a first embodiment of the apparatus is shown. This arrangement comprises a hood body or hood member 1 having two ends. The first end 2 has a substantially wide cross-section (diameter), and is funnel-shaped. During operation of this device, funnel end 2 is placed over the breast of the user. A second end 3 of the hood member constitutes a generally cylindrical extension of the funnel, and has a cross-section substantially narrower than the cross-section of the end 2. The second end 3 communicates with a collecting or catch chamber 4 and with a vacuum passage 5 via a short tubular extension 3a.

The vacuum passage 5 also communicates with a vacuum line 6, which in this embodiment is shown as a passage molded into the material of the hood. Ultimately, vacuum line 6 communicates with a vacuum pump 58, as by a base line or hose 53.

The collecting chamber 4 is arranged substantially immediately after the extension 3a of the hood. Separating means in the form of a depending separation wall 7 and a rear wall 8 of the hood member extension 3a form a baffle or trap to protect the vacuum line 6 from milk.

At the lower portion of the collecting chamber 4 is a valve mechanism 14, the details of which form no part of the current invention. As in the above-incorporated U.S. Pat. No. 4,857,051, the valve mechanism 14 cooperates with the collecting chamber 4 to allow a typical volume of milk expressed in a single stroke to collect without overflowing, with the action of the valve mechanism 14 being sufficiently quick to release the milk from the collecting chamber 4 into a container or receptacle 12 for the next stroke.

It has been discovered that milk can occasionally fill the collecting chamber 4 and overflow the rear wall 8 or similar structure, entering vacuum line 6. In order to prevent the milk from passing substantially further toward the vacuum pump 58, there is provided at least one porous body 20 (also see FIG. 1A) so disposed as to lie across the air passage that forms the fluid communication between the vacuum pump 58 and the hood 1. Accordingly, air being drawn by the vacuum pump 58 passes through the porous body 20.

In the preferred embodiment, the porous body 20 is disposed in a housing 60, releasably attached to the hood 1, as by reception in a connecting sleeve 10. An easily-releasable connection between the housing 60 and sleeve 10 is provided in the form of threads as shown, or the like, to permit easy removal for cleaning or other purposes, such as to use the housing 60 with other units.

Preferably, the housing 60 is openable, and for this purpose is most preferably constructed as a two-part housing including a first, upstream part 64 and a second, downstream part 66. Preferably, the first and second parts 64, 66 are connectible by a quick-release method such as the threads 68 shown in the embodiment of FIGS. 1 and 2 or the snap-fit formed by elements 70 shown in the embodiment of FIGS. 3 and 4. If desired, a thumb tab 71 (FIG. 1A) may be formed on one of the housing parts to aid in their separation.

When the apparatus is assembled as shown in FIG. 1, the air passage communicating the vacuum pump 58 and hood 1 is a continuous connection such that air being drawn by the pump 58 may exit the vacuum line 6, pass through the interior volume of the housing 60 and the porous body 20 therein, then through an air outlet of the housing 60, such as a nipple 59 and then to the pump 58.

The porous body 20 has at least two characteristics. First, it is substantially permeable to air at the pressures encountered in the apparatus in which it is used. Second, when contacted by human milk, it becomes impermeable to air at those pressures, at least at the places of contact.

In its presently preferred and disclosed form, the porous body 20 is in the form of a sheet of filter-like material fixed as by spot-welding within a downstream end of the downstream housing member 66. In order that it may be re-used, the porous body 20 may be made of a washable material such as polytetrafluoroethylene (PTFE).

A suitable material for the filter is presently available from Gelman Sciences, Inc. of Ann Arbor, Mich. and bears the Gelman designation TF-1000. This material has a porosity of 0.1 micron and is made of PTFE having a polypropylene backing. The housing 60 also may be made of polypropylene, and the filter may be heat welded in place in the housing my mating the polypropylene backing of the filter to the housing, then conducting a conventional heat welding operation.

In order to provide support for the porous body 20 and to provide for a desired form of air flow from the porous body 20 to the internal opening 59a of nipple 59, the rear wall of downstream member 66 is provided with a plurality of raised members such as ridges 72 or the like. The raised members 72 provide air channels 74 therebetween. The air channels 74 conduct air to the internal opening 59a.

In the disclosed embodiment, the raised members 74 have generally circular and concentric configurations, with the air channels 74 leading to a plurality of larger air channels 76 formed by discontinuities in the raised members 72. The larger air channels 76 lead to the internal opening 59a. If desired, a bridging member 78 may be disposed concentrically of the internal opening 59a to provide further support for the porous body 20.

In the disclosed embodiment, an internal wall 80 extends transversely within the housing 60, separating it respectively into first and second chambers 82, 84. The chambers 82, 84 are in flow communication through a communicating passage 86. preferably, the passage 86 is formed in a second nipple 88 extending into the first chamber 82 from the internal wall 80.

The internal wall 80 and second nipple 88 enhance the universality of the housing 60. When disconnected from a hood 1 having screw threads in a collar 10 of the type illustrated, the housing 60 may be connected to other types of breast contacting apparatus. For example, a hose may be interconnected between nipple 88 and the other type of breast contacting apparatus. As a further example, nipple 88 might be inserted directly into an opening in other apparatus that has been provided for that purpose. In this way, the housing also serves as an adaptor.

When nipple 88 has been connected by a hose or the like as described in the paragraph immediately above, milk from the other apparatus directly enters communicating passage 86 and then passes into the second chamber 84. However, when the housing 60 is connected to apparatus of the type illustrated, milk leaving the vacuum line 6 will enter the first chamber 82 at an upstream end 90 (FIG. 2) thereof. When a sufficient volume of milk collects, it will overflow into the communicating passage 86 and then enter the second chamber 84.

It is believed that, from the above, the operation of the apparatus and of the method of protecting the pump are apparent. Upon operation of the pump, air is drawn from the first end of the hood 1, through the vacuum passage 5, vacuum line 6, into the first chamber 82, through the communicating passage 86 and into second chamber 84, then through the porous body 20, internal opening 59a of nipple 59, and thence to the pump 58.

Should milk ever contact the porous body 20, the porous body 20 will become substantially impermeable to air, at least at the places of contact. Such contact, of course, would reduce the air flow and the effectiveness of the operation of the vacuum pump. Should sufficient milk reach the porous body 20, it may become substantially entirely impermeable to air. At such time, the effect of the vacuum pump within the hood 1 will substantially cease. Therefore, by using the pump of breast pump apparatus to draw operating air through a porous body of such porosity that the body constitutes a barrier to the passage of milk, one protects the pump from the milk.

Furthermore, because human milk does not penetrate through the porous body 20, the porous body 20 constitutes a barrier to the passage of milk across the air passage that communicates the pump 58 and the interior of the hood 1.

It is believed apparent that the application of the apparatus and method described above are not limited to the disclosed embodiments, but could be used with a great variety of breast pump apparatus and methods designed to subject the human breast to vacuum and that may result, intentionally or incidentally, in the expression of milk. The herein-incorporated U.S. Pat. No. 4,794,915 discloses one such method.

Furthermore, it is unimportant whether expressed milk is collected or discarded. For example, the container 12 of the illustrated embodiments may be omitted, and the expressed milk may be allowed to drain away. Accordingly, for purposes of the current invention, the collecting chamber 4 may be thought of as a drain for expressed milk interposed in the air passage between the vacuum pump 58 and the first end 2 of the hood 1, the porous body 20 being disposed downstream of the drain for the protection of the pump 58 and vacuum hose 53 leading to the pump.

Those skilled in this art will recognize further modifications of structure, arrangement, composition, methods and the like that can be made to the present invention, yet still fall within the scope of the invention as hereafter claimed.

What is claimed is:

1. Apparatus for pumping breastmilk, comprising:
   a breast contactor adapted to surround a portion of a woman's breast including the nipple, the breast contactor having means for receiving milk from the breast;
   a source of vacuum in fluid communication with said breast contactor through air passage means;
   a housing releasably connected to said air passage means; and
   a fluid barrier carried within said housing and disposed across said air passage means at a predetermined location, said barrier being permeable to air flow under the influence of said vacuum when dry and impermeable to air flow when wet, as by milk, said barrier completely blocking the flow of air through said air passage means when saturated and thereby blocking milk flow from said breast contactor to said source of vacuum.

2. The apparatus of claim 1, the fluid barrier being cleanable, the housing having a cover which is openable to expose said fluid barrier to allow cleaning of the fluid barrier.

3. The apparatus of claim 1, the fluid barrier comprising a washable filter.

4. The apparatus of claim 1, wherein said fluid barrier comprises a thin filter medium extending across an opening defined within said housing between an air inlet and an air outlet, said filter medium being exposed for cleaning when said housing is disconnected.

5. Apparatus comprising:
   a breast hood configured to receive at least the nipple of a human breast, the breast hood comprising means for receiving milk from a breast and directing the received milk to an outlet thereof;
   a vacuum pump;
   an air line in fluid communication with the vacuum pump and the breast hood for withdrawing air from the breast hood;
   a milk drain intermediate the breast hood and the vacuum pump, disposed for handling milk passing from the breast hood;
   a housing releasably connected in said air line, a fluid barrier carried by said housing such that air passing from the breast hood toward the vacuum pump passes through the fluid barrier,
   said fluid barrier, when dry and under the influence of said vacuum pump, being substantially permeable to air, and when wet with human milk and under the influence of said vacuum pump, being substantially impermeable to air where wetted.

6. The apparatus of claim 5, the fluid barrier comprising a filter.

7. The apparatus of claim 5, the fluid barrier comprising a polytetrafluoroethylene filter.

8. The apparatus of claim 5, said fluid barrier comprising a filter medium disposed within the housing and extending across an opening defined therein, the housing having a cover which is openable for access to the filter.

9. A method of restraining the passage of milk beyond a selected place in a breast pump apparatus, the method comprising the steps of:
   providing a breast receiver configured to receive at least the nipple of a human breast;

providing a source of vacuum in fluid communication with the breast receiver through an air flow line;

at said selected place, providing a fluid barrier to the passage of human milk contained within a housing releasably connected in said air flow line, said fluid barrier being permeable to air when dry and impermeable to air when wet, as by milk;

contacting a human breast with the breast receiving portion;

operating the source of vacuum to withdraw air from the breast receiver; and operating the source of vacuum to draw air through the milk barrier.

10. In a breastpump for pumping mother's milk having a hood body for placement over a breast including a main funnel portion within which the breast and breast nipple are received, a container for receiving milk expressed from the breast in fluid communication with the funnel portion, and a source of intermittent vacuum in fluid communication with the funnel portion through an air passage to effect milk expression, the improvement comprising:

a milk barrier located in and extending across the air passage, said barrier being formed of a porous material which is permeable to air when dry and impermeable to air when wet, as by milk, said barrier substantially completely blocking all fluid flow through the air passage when saturated by milk to thereby protect the vacuum source from milk, said barrier being carried by a housing releasably connected in said air passage.

11. The improved breastpump of claim 10 wherein said barrier is a filter medium, said housing defining an opening therein which opening is covered by said filter medium.

12. The improved breastpump of claim 11 wherein said housing includes a foraminous filter medium support surface upon which said filter medium is supported.

13. The improved breastpump of claim 12 wherein said foraminous surface comprises a plurality of ridges formed in a base wall of said housing defining air channels in said support surface which connect with the air passage, said filter medium being supported upon said ridges.

14. The improved breastpump of claim 13 wherein said base wall is formed on a portion of said housing which is removable from said housing for cleaning of said filter medium.

* * * * *

UNITED STATES PATENT AND TRADEMARK OFFICE
CERTIFICATE OF CORRECTION

PATENT NO. : 5,071,403
DATED : December 10, 1991
INVENTOR(S) : Karl O.A.H. Larsson It is certified that error appears in the above-identified patent and that said Letters Patent is hereby corrected as shown below:

In column 4, line 66, please delete "preferably" and substitute therefor --Preferably--.

IN THE CLAIMS

In claim 1, line 8, after "connected" please delete "to" and substitute therefor --in--.

In claim 5, line 50, please delete "w hen" and substitute therefor --when--.

Signed and Sealed this

Twenty-second Day of June, 1993

Attest:

MICHAEL K. KIRK

Attesting Officer

Acting Commissioner of Patents and Trademarks